US00PP11374P

United States Patent [19]

Leue

[11] Patent Number: Plant 11,374

[45] Date of Patent: May 9, 2000

[54] DOUBLE IMPATIENS PLANT NAMED 'BFP-13357'

[75] Inventor: Ellen F. Leue, DeKalb, Ill.

[73] Assignee: Ball Flora Plant, a division of Ball Horticultural Company, West Chicago, Ill.

[21] Appl. No.: 09/113,134

[22] Filed: Jul. 9, 1998

[51] Int. Cl.[7] ..... A01H 5/00

[52] U.S. Cl. ..... Plt./317

[58] Field of Search ..... Plt./317

[56] References Cited

U.S. PATENT DOCUMENTS

P.P. 10,033 9/1997 Greinke ..... Plt./317

*Primary Examiner*—Howard J. Locker
*Assistant Examiner*—Kent L. Bell
*Attorney, Agent, or Firm*—C. A. Whealy

[57] ABSTRACT

A new and distinct cultivar of Double Impatiens plant named 'BFP-13357', characterized by its numerous and consistently double, orange red and white bi-colored flowers; compact and mounded plant habit; and dark green leaves.

1 Drawing Sheet

BACKGROUND OF THE INVENTION

The present invention relates to a new and distinct cultivar of Double Impatiens plant, botanically known as *Impatiens walleriana*, and hereinafter referred to by the cultivar name 'BFP-13357'.

The new Double Impatiens is a product of a planned breeding program conducted by the Inventor in Arroyo Grande, Calif. The objective of the breeding program was to develop new cultivars with excellent basal branching, upright and medium growth habit, numerous large flowers, and interesting flower and foliage colors.

The new Double Impatiens originated from a cross made by the Inventor of the proprietary *Impatiens walleriana* selection 00012-3-3-1 as the male, or pollen parent, with the proprietary *Impatiens walleriana* selection 00343-2 as the female, or seed parent. The cultivar 'BFP-13357' was discovered and selected by the Inventor as a flowering plant within the progeny of the stated cross in a controlled environment in Arroyo Grande, Calif., on Sep. 15, 1996.

Asexual reproduction of the new cultivar by terminal cuttings taken at Arroyo Grande, Calif., has shown that the unique features of this new Double Impatiens are stable and reproduced true to type in successive generations of asexual reproduction.

SUMMARY OF THE INVENTION

The following traits have been repeatedly observed and are determined to be the unique characteristics of 'BFP-13357'. These characteristics in combination distinguish 'BFP-13357' as a new and distinct cultivar:

1. Numerous and consistently double, orange red and white bi-colored flowers.

2. Compact and mounded plant habit.

3. Dark green leaves.

The new Double Impatiens can be compared to the cultivar 'Cherry Vanilla', disclosed in U.S. Plant Pat. No. 10,033. However, in side-by-side comparisons conducted by the Inventor in Arroyo Grande, Calif., plants of the new Double Impatiens differ from plants of the cultivar 'Cherry Vanilla' in the following characteristics:

1. Plants of the new Double Impatiens are more compact and have shorter internodes than plants of the cultivar 'Cherry Vanilla'.

2. Plants of the new Double Impatiens have smaller leaves than plants of the cultivar 'Cherry Vanilla'.

3. Flower color of plants of the new Double Impatiens is more orange than flower color of plants of the cultivar 'Cherry Vanilla'.

4. Plants of the new Double Impatiens have much shorter peduncles than plants of the cultivar 'Cherry Vanilla'.

A detailed comparison of plants of the cultivar BFP-13357 and the cultivar 'Cherry Vanilla' appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of 'BFP-13357'. Flower and foliage colors in the photograph may appear different from the actual colors due to light reflectance.

DETAILED BOTANICAL DESCRIPTION

The cultivar 'BFP-13357' has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 22° C. and night temperatures about 18° C.

In the following description, color references are made to The Royal Horticultural Society Colour Chart except where general terms of ordinary dictionary significance are used.

Botanical classification: *Impatiens walleriana* cultivar 'BFP-13357'.

Parentage:

*Male parent.*—Proprietary *Impatiens walleriana* selection 00012-3-3-1.

*Female parent.*—Propietary *Impatiens walleriana* selection 00343-2.

Propagation:

*Type cutting.*—Terminal cuttings.

*Time to initiate roots.*—About 7 days at temperatures about 18° C.

*Time to develop roots.*—About 21 days at temperatures about 18° C.

*Rooting habit.*—Fibrous, fine, freely branching.

Plant description:

*Plant form.*—Compact and mounded.

*Growth and branching habit.*—Moderately vigorous. Basal branching with about four lateral branches at the base, dense and bushy growth. Appropriate for 10 and 12.5-cm containers.

*Plant height.*—About 12 cm.

*Crop time.*—About eight weeks are required to produce a finished flowering plant in a 10-cm container from a rooted cutting.

*Lateral branches.*—Length: About 11 cm. Diameter: About 5 mm. Internode length: About 2.1 cm. Color: 146A with dark reddish, 183C, streaks.

*Foliage description.*—Leaves simple, generally symmetrical, abundant, alternate. Quantity of leaves per lateral branch: About 27. Length: About 4.4 cm. Width: About 2.6 cm. Shape: Ovate with acuminate apex, cuneate to attenuate base and crenate/ciliate margin. Texture: Smooth, glabrous. Color: Fully expanded foliage, upper surface: 139A. Fully expanded foliage, lower surface: 139C with dulled red, 182A, spots. Petiole: Length: About 1 cm. Diameter: About 2 mm. Color: 146A with dark reddish, 183C, streaks.

Flower description:

*Flower type and habit.*—Numerous and consistently double orange red and white bi-colored flowers. Flowers buds open similar to a rose in fullness. Freely and continuously flowering. Flowers arise from leaf axils. Usually about 14 flowers and flower buds per lateral branch. Flowers positioned slightly above the foliage and typically face outward and upright. Flowers not persistent.

*Flowering season.*—Year-round under greenhouse conditions. In the garden, flowering is continuous from spring until fall.

*Flower longevity.*—About 7 to 8 days.

*Flower size.*—Diameter: About 4 cm. Depth (height): About 2 cm.

*Flower buds.*—Length: About 1.5 cm. Diameter: About 1.1 cm. Shape: Ovoid. Color: Initially light green becoming 36C before opening.

*Petals.*—Quantity: Numerous, about 18 to 27 per flower. Length: About 2.5 cm. Width: About 1.6 cm. Shape: Rounded to cordate with rounded or emarginate apex, attenuate base and entire margin. Texture: Smooth, iridescent. Color: Fully opened, upper surface: Bi-colored, orange red, 33A, and white, 155D. Fully opened, lower surface: Bi-colored, orange red, 40C, and white, 155D.

*Spur.*—Length: About 2.7 to 3.2 cm. Color: 179D.

*Peduncles.*—Length: About 2 cm. Angle: Upright or outward. Strength: Moderately strong. Color: 145B.

*Reproductive organs.*—None observed.

Disease resistance: Under commercial conditions, resistance to pathogens has not been observed.

Seed development: Seed production has not been observed.

CHART A

| CHARACTERISTIC | 'BFP-13357' | 'CHERRY VANILLA' |
|---|---|---|
| PLANT HEIGHT | About 12 cm | About 15 cm |
| LATERAL BRANCH LENGTH | About 11 cm | About 13 cm |
| LATERAL BRANCH DIAMETER | About 5 mm | About 7 mm |
| INTERNODE LENGTH | About 2.1 cm | About 3 cm |
| LEAF LENGTH | About 4.4 cm | About 5.5 cm |
| LEAF WIDTH | About 2.6 cm | About 3.8 cm |
| LEAF COLOR, UPPER SURFACE | 139A | 147A |
| LEAF COLOR, LOWER SURFACE | 139C with dulled red, 182A, spots | 147B with dark red, 183C, spots |
| PETIOLE LENGTH | About 1 cm | About 2 cm |
| PETIOLE DIAMETER | About 2 mm | About 3 mm |
| PETAL COLOR, UPPER SURFACE | 33A and 155D | 45A and 155D |
| PETAL COLOR, LOWER SURFACE | 40C and 155D | 43B and 155D |
| PEDUNCLE LENGTH | About 2 cm | About 4 cm |

It is claimed:

1. A new and distinct cultivar of Double Impatiens plant named 'BFP-13357', as illustrated and described.

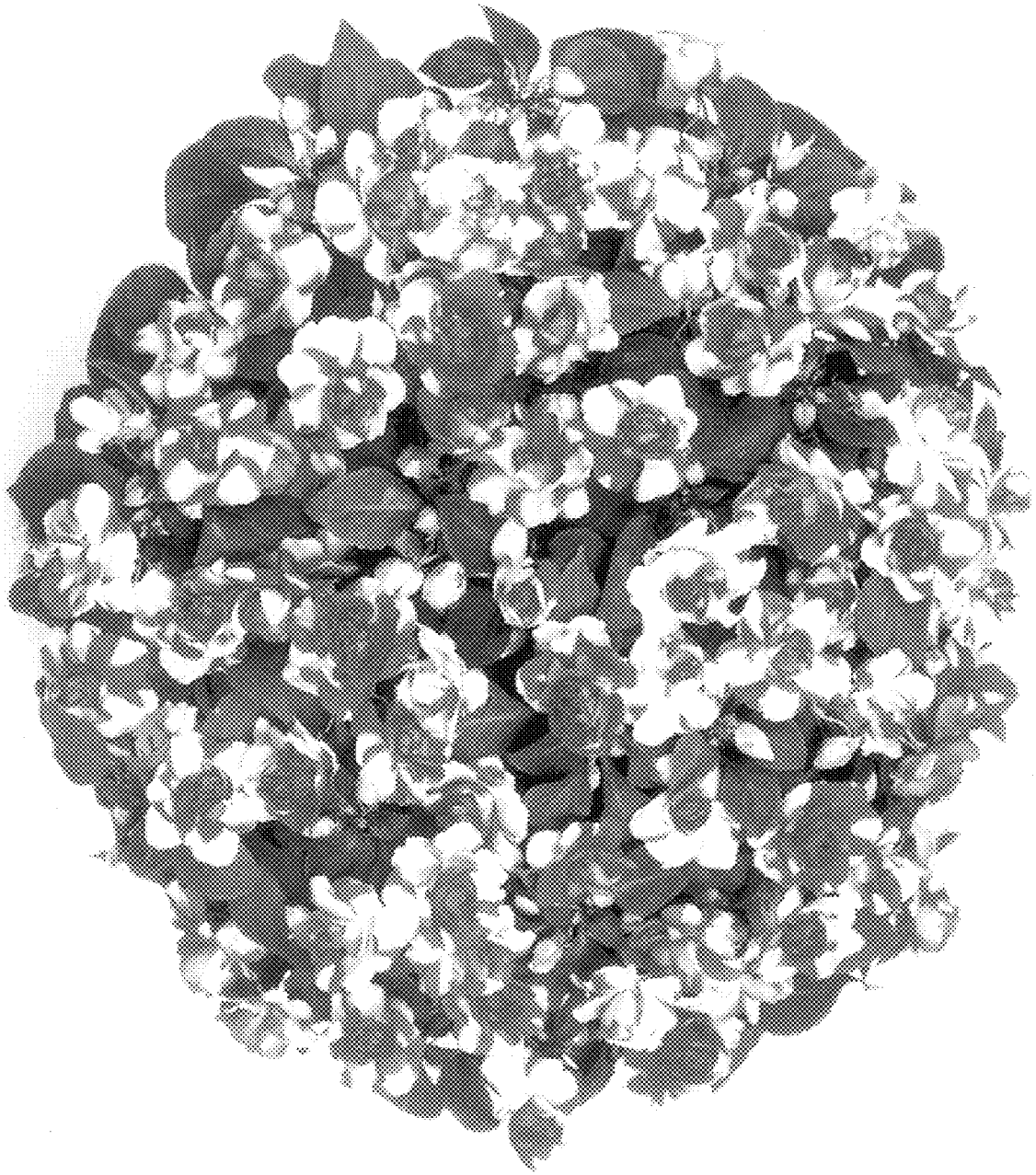

* * * * *